United States Patent
Potyrailo et al.

(10) Patent No.: US 8,159,347 B2
(45) Date of Patent: Apr. 17, 2012

(54) SENSORS HAVING GAP BASED SENSING DEVICES AND METHODS OF MAKING AND USING THE SAME

(75) Inventors: Radislav Alexandrovich Potyrailo, Niskayuna, NY (US); William Guy Morris, Rexford, NY (US); Cheryl Margaret Surman, Albany, NY (US); Katharine Dovidenko, Rexford, NY (US); Tracy Lynn Paxon, Waterford, NY (US)

(73) Assignee: General Electric Company, Niskayuna, NY (US)

(*) Notice: Subject to any disclaimer, the term of this patent is extended or adjusted under 35 U.S.C. 154(b) by 721 days.

(21) Appl. No.: 12/237,571

(22) Filed: Sep. 25, 2008

(65) Prior Publication Data

US 2010/0073135 A1 Mar. 25, 2010

(51) Int. Cl.
*G08B 13/14* (2006.01)
(52) U.S. Cl. ............................. 340/572.1; 340/572.7
(58) Field of Classification Search .... 340/572.1–572.8, 340/10.1; 235/435, 439; 343/700 R, 701
See application file for complete search history.

(56) References Cited

U.S. PATENT DOCUMENTS

| | | | |
|---|---|---|---|
| 7,056,446 B2 | 6/2006 | Nagase et al. | |
| 7,647,109 B2 * | 1/2010 | Hastings et al. | 607/32 |
| 2004/0094414 A1 | 5/2004 | Engelhardt et al. | |
| 2005/0110064 A1 | 5/2005 | Duan et al. | |
| 2005/0136419 A1 | 6/2005 | Lee | |
| 2005/0227373 A1 | 10/2005 | Flandre et al. | |
| 2005/0248356 A1 | 11/2005 | Care | |
| 2006/0154400 A1 | 7/2006 | Choi et al. | |
| 2006/0226985 A1 | 10/2006 | Goodnow et al. | |
| 2007/0075148 A1 | 4/2007 | Usami | |
| 2007/0090927 A1 | 4/2007 | Potyrailo et al. | |
| 2007/0292601 A1 | 12/2007 | Nuckolls et al. | |
| 2008/0121045 A1 | 5/2008 | Cole et al. | |
| 2008/0234599 A1 | 9/2008 | Chiao et al. | |
| 2008/0284599 A1 * | 11/2008 | Zdeblick et al. | 340/572.1 |

FOREIGN PATENT DOCUMENTS

WO 2007046582 A1 4/2007
WO 2007120312 A2 10/2007

OTHER PUBLICATIONS

PCT/SE2009/051055, Search Report, Dec. 21, 2009.
PCT/SE2009/051055, Written Opinion, Dec. 21, 2009.

* cited by examiner

*Primary Examiner* — Toan N Pham
(74) *Attorney, Agent, or Firm* — Jenifer E. Haeckl

(57) ABSTRACT

A sensor is provided. The sensor comprises at least one sensing device comprising a first electrode and a second electrode, and a gap defined as a distance between one or more facing inner surfaces of the first and second electrodes, wherein the gap distance at least in part determines a threshold of one or more sensed parameters, and an antenna in operative association with the sensing device.

26 Claims, 6 Drawing Sheets

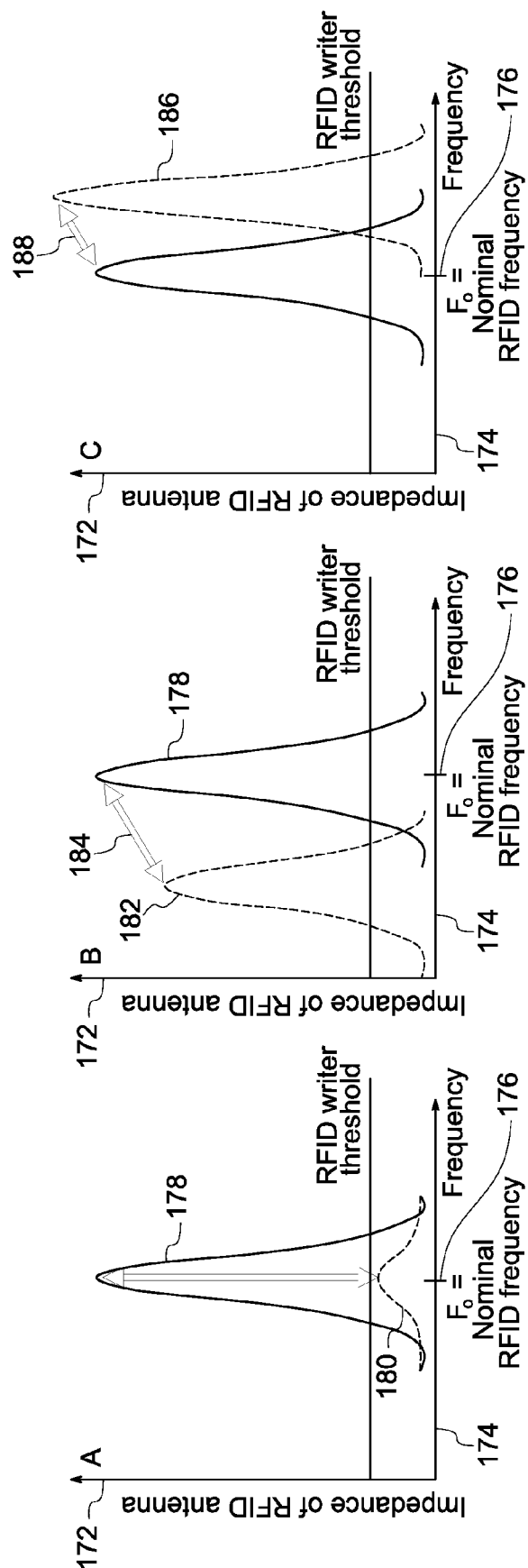

SENSORS HAVING GAP BASED SENSING DEVICES AND METHODS OF MAKING AND USING THE SAME

BACKGROUND

The invention relates to sensors, and more particularly to chemical, physical or biological sensors.

Conventionally, radio frequency identification (RFID) tags are used for asset tracking. For example, RFID tags may be used for tracking the removal of objects from a location and the replacement of the objects at the location. The RFID tags have been combined with a biometric reader. Such RFID circuit uses certain functional blocks for processing both the biometric signals and the RFID signals. RFID tags can have unique numbers and can be used to read these identification numbers with information related to the article to which the tag is attached. RFID tags are also used for detecting the unauthorized opening of containers and baggage. RFID tags can be included in a variety of articles such as postage stamps and other mailing labels, garments, and numerous other articles. RFID systems have been recently applied for wireless sensing applications such as RFID-based temperature sensors.

These and other properties of RFID tags can be used to form sensors that can detect chemical, biological and physical properties.

BRIEF DESCRIPTION

In one embodiment, a sensor is provided. The sensor comprises at least one sensing device comprising a first electrode and a second electrode, and a gap defined as a distance between one or more facing inner surfaces of the first and second electrodes, wherein the gap distance at least in part determines a threshold of one or more sensed parameters, and an antenna in operative association with the sensing device.

In another embodiment, a radio frequency based sensor is provided. The sensor comprises a sensing gap defined by two or more electrodes, and an antenna in operative association with the sensing gap and the electrodes.

In yet another embodiment, a method of making a sensor is provided. The method comprises providing an antenna having one or more turns, and forming a sensing gap comprising first and second electrodes and defined by a distance between one or more facing inner surfaces of the first and second electrodes, wherein the gap distance at least in part determines a threshold of one or more sensed parameters, and wherein the sensing gap is in operative association with the antenna.

DRAWINGS

These and other features, aspects, and advantages of the present invention will become better understood when the following detailed description is read with reference to the accompanying drawings in which like characters represent like parts throughout the drawings, wherein:

FIGS. 10-12 are graphical representations of detection principle of the sensor.

These and other features, aspects, and advantages of the present invention will become better understood when the following detailed description is read with reference to the accompanying drawings in which like characters represent like parts throughout the drawings, wherein:

DETAILED DESCRIPTION

Embodiments of the present technique relate to sensors having at least one sensing device. The sensing device has a first electrode and a second electrode. The sensing device further includes a gap defined as a distance between one or more facing inner surfaces of the first and second electrodes. The gap distance at least in part determines a threshold of one or more sensed parameters. The sensed parameters may include physical parameters (for example, pressure), chemical parameters (for example, pH, glucose level, gases), and biological parameters (for example, viruses, proteins, DNA).

The sensing device having the gap may be in electrical communication with an antenna. The sensing device may be in series or parallel electrical connection with the antenna. In certain embodiments, the sensor may be wireless, or wired, or electronic, (radio frequency identification) RFID based, non-RFID based, or combinations of two or more. In embodiments where the sensor is a RFID based sensor, the sensor may be a wireless sensor. Also, the RFID based sensor may include a passive RFID tag, or a semi-passive RFID tag, or an active RFID tag. Further, the RFID tags may be configured to operate at frequencies ranges, such as but not limited to, low frequency range from about 125 KHz to about 135 KHz, high frequency range of about 13.56 MHz, ultra high frequency (UHF) range from about 850 MHz to about 960 MHz, and microwave frequency range of about 2.45 GHz-5.8 GHz.

Figure 1:
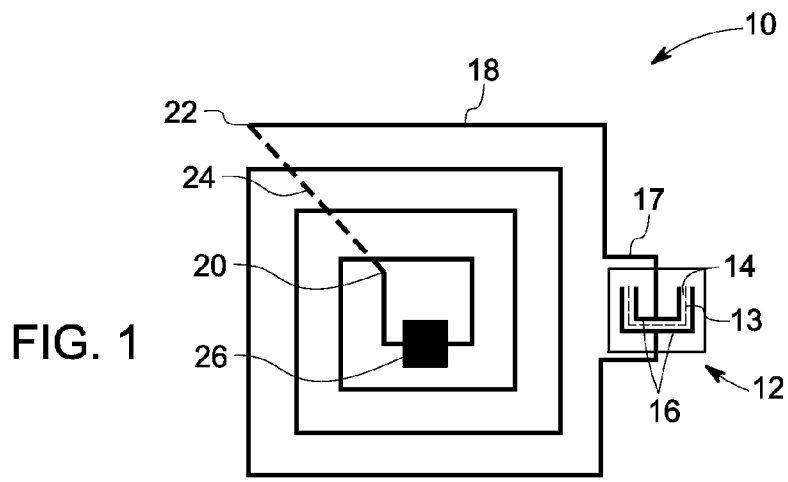
FIGS. 1-3 are schematic representations of sensors having a separate sensing device in electrical communication with the antenna.
Figure 2:
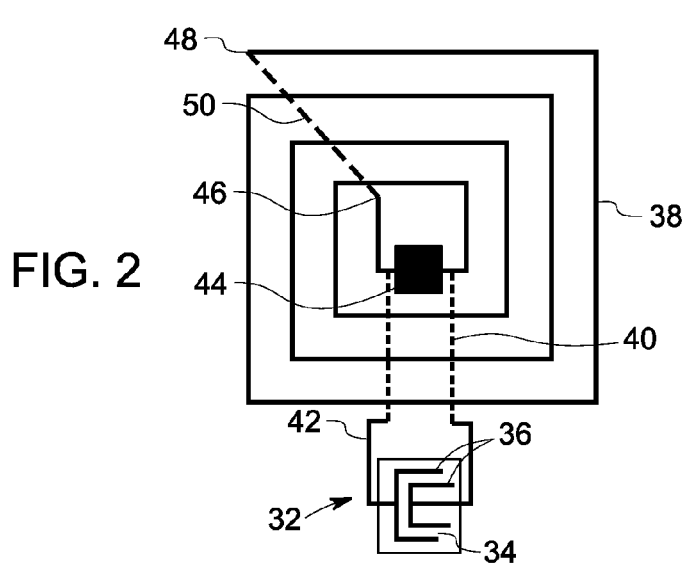
Figure 3:
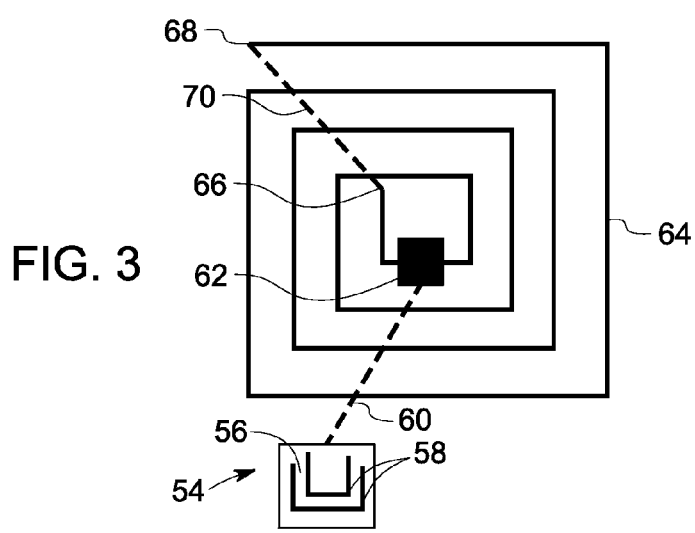
Figure 4:
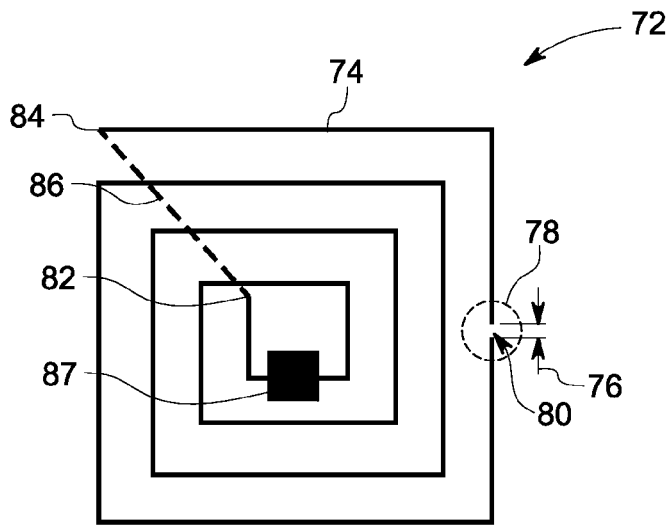
FIGS. 4-6 are schematic representations of a sensor where a portion of an antenna is configured to act as a sensing device.
Figure 5:
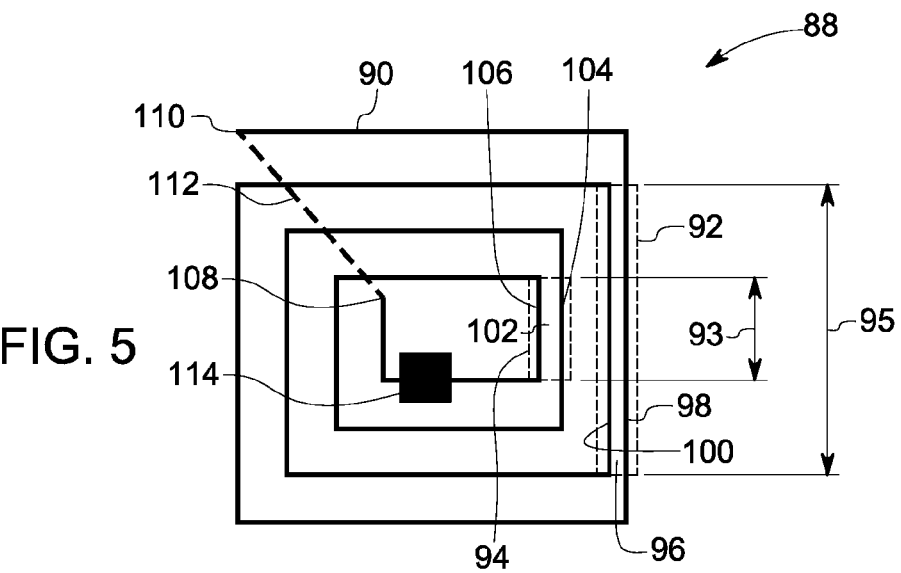
Figure 6:
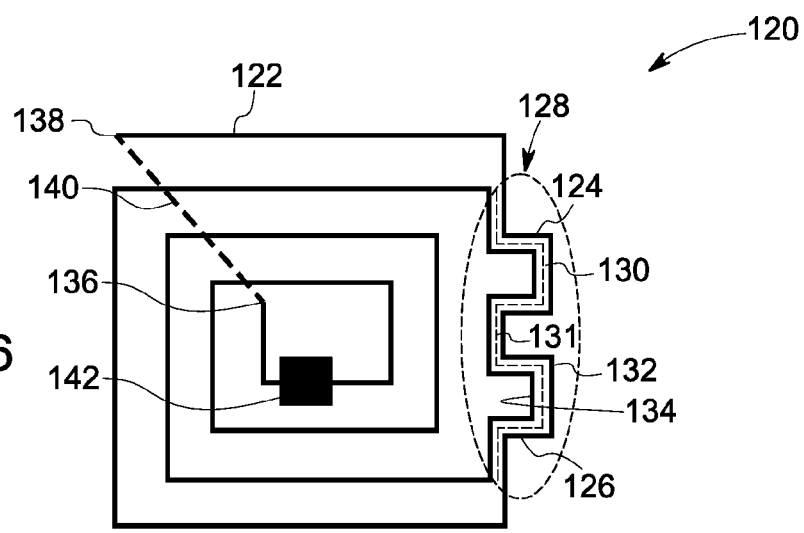

In certain embodiments, a RFID tag may be converted into a RFID sensor. In these embodiments where the RFID tags are converted into RFID sensors, a sensing device having a gap is incorporated into the RFID tag. In these embodiments, a gap configured to act as a sensing region may be provided on the RFID tag such that the gap is in operative association with an antenna of the RFID tag. As illustrated in FIGS. 1-3, the gap may be a separate entity from the antenna of the RFID tag. Alternatively, as illustrated in FIGS. 4-6, the gap may be a part of the antenna. Although not illustrated, embodiments illustrated in FIGS. 1-6 may include two or more sensing devices. In some embodiments, the size of the antenna may be in a range from about 0.5 millimeters×0.5 millimeters to about 100×100 millimeters. In one embodiment, the size of the antenna may be about 10 millimeters×10 millimeters.

Typically, when the a portion of the antenna is configured to act as the sensing device, the spacing between the antenna turns or windings in these portions may be in a range of about 0.005 microns to about 500 microns. In one embodiment, the spacing between the windings of the antenna in the portion that is configured to act as a sensing device is about 25 microns.

Upon incorporation of the sensing device in the RFID tag, the electrical response of the sensor may be one or more of a resistance change, a capacitance change, a combination of resistance and capacitance change. In one embodiment, by incorporation of the sensing device in the RFID tag, electrical response of the RFID sensor is translated into resonance change of the complex impedance response of the antenna. The signal from the RFID tag is reflected by one or more of a change in the resonance properties of the complex impedance of the antenna, or appearance or disappearance of digital ID of the RFID tag reading with a digital reader/writer. As used herein, the term "digital reader/writer" is a device that reads digital information from a memory chip of the RFID tag and writes user-defined digital information to the memory chip. The digital reader/writer may also be referred to as "reader" or "interrogator" or "writer" in this application. In some embodiments, addition of the sensing device in the RFID tag may result in the formation of a resonant sensing structure. In these embodiments, an environmental change affects the resonance of the sensor. Digital writer writes a time sequence of data into memory chip. If the resonance of the sensor is changed due to the sensing device, such that the resonance frequency position is outside the frequency range of writing the digital data, and/or the resonance magnitude is outside the range of magnitudes (smaller or larger) of writing the digital data, the certain values are not written into chip, thus permanently storing time-sequence data. For time-critical applications where there is a need to track the time of exposure of the sensor to the environment, digital data is recorded onto the chip only when a parameter of interest exceeds the threshold.

In one embodiment, the digital reader/writer device can be combined with the scanner of impedance of the resonant sensor to determine the properties of the sensor resonance. As used herein, the term "scanner of impedance of the resonant sensor" is a device that scans frequencies across the resonance of the sensor and determines the properties of the sensor resonance. Non-limiting examples of properties of the sensor resonance may include width, shape, symmetry of shape, peak height, and peak position of the complex impedance signal.

When the digital reader/writer device is combined with the scanner of impedance of the resonant sensor, data stored in the memory of the memory chip of an RFID sensor can contain at least one property of the sensor resonance (for example, the width, shape, symmetry of shape, peak height, and peak position of complex impedance signal). This sensing information is stored with a time-sequence of data into memory chip. The sensing information is not a one-bit information (on-off response) but quantitative information with an information resolution limited not by the sensor, but by the scanner of impedance of the resonant sensor.

The shape of the sensing gap may include a slot, an array of slots, a morphology-induced shape, a serpentine shape, a coil, a fractal, or combinations thereof. In certain embodiments, the gap may be in the form of a channel, an interdigital electrode structure, a three-dimensional (3-D) electrode structure, or combinations thereof. In certain embodiments, the gap may include a zero-dimensional gap structure, a one-dimensional gap structure, a two-dimensional gap structure, a three-dimensional gap structure. The zero-dimensional gap structure is a gap structure formed by electrodes with a relatively small cross section, such that the gap between the electrodes is small enough to fit only one target species (for example only one spore, only one bacterium, etc.). The one-dimensional gap structure is a gap structure formed by electrodes with a relatively small cross section in one direction such that the gap is small enough to fit only one-dimensional array of target species (for example spores or bacteria in a line). The two-dimensional gap structure is a gap structure formed by electrodes with a small cross section in two directions. The three-dimensional gap structure is a gap structure formed by electrodes with a small cross-section in three directions. The structure of the gap may also vary depending on the ease of fabrication and also based on the physical property and/or chemical and/or biological species that needs to be detected.

In certain embodiments, a material present in of the gap may include metals, organic material, semiconductor materials, organic electronics materials, dielectric materials, or combinations thereof. In some embodiments, the gap may include sensing materials for detection of chemical, biological, and/or physical changes around the gap sensor. Non-limiting examples of the sensing materials in the gap region includes nanowires, nanofibers, nanoparticles, formulated materials with functional additives, doped conjugated polymers, inorganic materials, organic materials, polymeric materials, biological materials, living cells, biological molecule receptors, antibodies, aptamers, nucleic acids, biological molecules functionalized with metal particles, biological molecules functionalized with polymer particles, biological molecules functionalized with silica particles and any other known sensing materials and their combinations that produce detectable change in resistance and/or capacitance upon chemical, biological, and/or physical changes around the sensing device.

In other embodiments, the gap may be substantially free of the electrode material. In embodiments where the gap does not contain any sensing material, the signal change may originate from the change in sample composition in the gap. Non-limiting examples of changes of sample composition include water vapor concentration in air (relative humidity) or any other gas, ions concentration in water (e.g., de-ionized water versus drinking water versus sea water), organic matter concentration in wastewater, biological matter (e.g., bacteria, cells, viruses) concentration in water In certain embodiments, the distance between the facing inner surfaces of the first and second electrodes may be in a range of about few nanometers to about thousands of nanometers. In one embodiment, the gap distance is in a range of about 2 nanometers to about 10000 nanometers. The gap distance may be determined based on the parameter that needs to be detected. For example, the gap distance may be determined based on the size of the biological properties that needs to be detected. In another example, the gap distance may be larger for detecting bacteria that are typically few tens of microns in size, whereas the gap distance may be smaller for detecting viruses that are few tens of nanometers.

In one embodiment, the first electrode, or the second electrode, or both have a continuous surface. For example, the first or second electrode may be a continuous rectangle, a square, a circle, or any other geometric shape. In another embodiment, the first or second electrode may have a discontinuous surface. For example, the first or second electrode may have a patterned surface, such as grid, a surface having holes, wherein the holes may or may not be through holes, a surface having protruding structures, or combinations thereof. Further, the first and second electrodes may have same or different kinds of surfaces. In one embodiment, a dielectric material may be applied to one or more exposed surfaces of the first electrode, or the second electrode, or both to prevent the electrodes from shorting out when the sensor is exposed to a conductive fluid.

In certain embodiments, the electrode material may be capable of transporting electrical current with determined electrical properties. Nonlimiting examples of electrode materials include metals such as copper, aluminum, gold, silver, alloys of copper (e.g. brasses, bronzes), alloys of aluminum (e.g. Nambe™, Silumin™), alloys of gold (e.g. Electrum™), conducting polymers, doped conducting polymers, such as doped polyacetylene, doped polyaniline, doped polythiophene, carbon nanotubes, carbon fibers, carbon particles, carbon paste, conducting inks, or combinations thereof.

In one embodiment, the electrical resistance of the electrode material is less than about 100 Ohms. In another embodiment, the electrical resistance of the electrode material is less than about 50 ohms, or less than about 0.5 ohms. Whereas, the electrical resistance of the antenna structures may be in a range from about 0.5 Ohms to less than 100 Ohms.

In certain embodiments, a method of making the sensor may include providing an antenna having one or more turns. Further, a sensing gap including the first and second electrodes is fabricated. In certain embodiments, the antenna may be fabricated by employing techniques, such as microlithography and/or nanolithography. The sensing gap or sensing device may be fabricated by employing techniques, such as but not limited to, self-assembly, roll-to-roll process, lithography, liquid deposition, milling, focused ion beam milling, or microlithography. In one embodiment, the first and second electrodes may be formed by a batch manufacturing process. In embodiments where a portion of the antenna is configured to act as a sensing device, the gap may be fabricated separately by employing the above listed techniques. In embodiments where the sensing device is a separate entity from the antenna, the sensing device may be fabricated separately and subsequently coupled to the antenna. Further, the sensing device may be coupled to the antenna in parallel or series electrical connection by employing the above listed fabrication techniques. In one embodiment, the sensor may be disposed on a silica surface, such that the silica surface within the gap does not contain any surface modifications for nonspecific binding of molecules and molecular assemblages.

Referring now to FIG. 1, the sensor 10 includes a sensing device 12 having a gap 14 between the facing inner surfaces of the two electrodes 16 and a gap length 13 defined as the distance along the two electrodes 16. The sensing device 12 is electrically coupled to the antenna 18 by employing connectors 17. In the illustrated embodiment of FIG. 1, the sensing device 12 and the antenna 18 are in series connection. In one example, the connectors 17 may be electrically conducting cables, wires, strips, or the like. The sensor 10 further includes an antenna 18 having two ends 20 and 22. The ends 20 and 22 of the antenna are electrically connected using a conductor medium 24 (such as a conductor wire, a conductor strip, or a conductor cable) in such a way that the conductor medium 24 does not electrically short out the other regions of the antenna 18 that this conductor medium crosses. The memory chip 26 is used for storing information. The chip 26 may be activated by the radio frequency signal transmitted from the read/write unit. The antenna 18 of the sensor 10 receives and transmits signals. The signals transmitted by the antenna 18 are picked up by the pick-up coil or the reader (not shown) that is disposed in operative proximity of the sensor 10. The pick up coil may be a part of the reader. In one example, the sensor 10 and the pick-up coil may be coupled via inductive coupling. Alternatively, in another embodiment, the sensor 10 and the pick-up coil are not necessarily coupled via electrical contacts. In such embodiments, the sensor 10 and the pick-up coil may be adapted to communicate wirelessly.

As shown in FIG. 2, a sensor 30 includes a sensing device 32 having a gap 34 defined by electrodes 36. The sensing device 32 is electrically coupled to the antenna 38 by employing electrical conductors 40. The electrical conductors 40 in turn are coupled to the sub-connectors 42 that are directly coupled to the sensing device 32. In one embodiment, the electrical conductors 40 and the sub-connectors 42 may be the same, that is the electrical conductors 40 and the connectors 42 may form a continuous body of connecting medium. In another embodiment, the electrical conductors 40 and the connectors 42 may be the different physical entities. The sensor 30 also includes a memory chip 44. Further, the two ends 46 and 48 of the antenna 38 are electrically connected using a conductor medium 50 (such as a conductor wire, a conductor strip, or a conductor cable) in such a way that the conductor medium does not electrically short out the other regions of the antenna 38 that this conductor medium crosses.

Turning now to FIG. 3, a sensor 52 includes a sensing device 54 having a gap 56 defined by electrodes 58. The sensing device 54 is electrically coupled to the memory chip 62 by employing electrical conductors 60. The electrical connection between the sensing device 54 and the memory chip 62 is performed via analog input in the memory chip. The memory chip 62 in turn is coupled to the antenna 64. Two ends 66 and 68 of the antenna 64 are electrically connected using a conductor medium 70 (such as a conductor wire, a conductor strip, or a conductor cable) in such a way that the conductor medium 70 does not electrically short out the other regions of the antenna 64 that this conductor medium crosses.

FIGS. 4-6 illustrate embodiments where a portion of the antenna is configured to act as a sensing device. In the illustrated embodiment of FIG. 4, a sensor 72 includes an antenna 74. A portion 78 of the antenna 74 is configured to act as a sensing device 80. The portion 78 of the antenna 74 contains a discontinuity in the antenna that acts as the gap 76 for the sensing device 80. Although not illustrated, there may be two or more such gaps in the antenna 74. The antenna 74 further includes two ends 82 and 84 that are electrically connected using a conductor medium 86. The sensor 72 further includes a memory chip 87.

FIG. 5 illustrates a sensor 88 having an antenna 90. The antenna 90 includes two sensing devices, namely, a first sensing device 92 and a second sensing device 94. The first sensing device 92 includes a first gap 96 formed between the portions of the windings 98 and 100 and having a gap length 95. Similarly, the second sensing device 94 includes a second gap 102 formed between the portions of the windings 104 and 106 and having a gap length 93. As illustrated, the distances between the windings 98 and 100, and 104 and 106 are relatively smaller than the distances between the remaining windings of the antenna 90. These lower distances enable the formation of sensing devices 92 and 94. The antenna 90 further includes two ends 108 and 110 that are electrically connected using a conductor medium 112. The sensor 88 further includes a memory chip 114.

FIG. 6 illustrates a sensor 120 employing an antenna 122. The protruded portions 124 and 126 are configured to act as a single sensing device 128. The sensing device 128 includes a gap 130 having a gap length represented by the dotted line 131 and confined between the winding portions 132 and 134. The gap 130 continues from one protrusion 124 to the other 126. The antenna 122 further includes two ends 136 and 138 that are electrically connected using a conductor medium 140. The sensor 120 further includes a memory chip 142. Compared to the individual gap lengths 95 and 93 of the sensing devices 92 and 94, respectively (see FIG. 5), the gap length 131 of the sensing device 128 is longer, there by providing an increased sensing area. In biological detection of bacteria, spores or viruses, the longer gap provides a higher probability of capturing the target species within the gap. In chemical detection of gases and liquids, the longer gap provides a larger signal response due to the increased sensing area.

Figure 7:
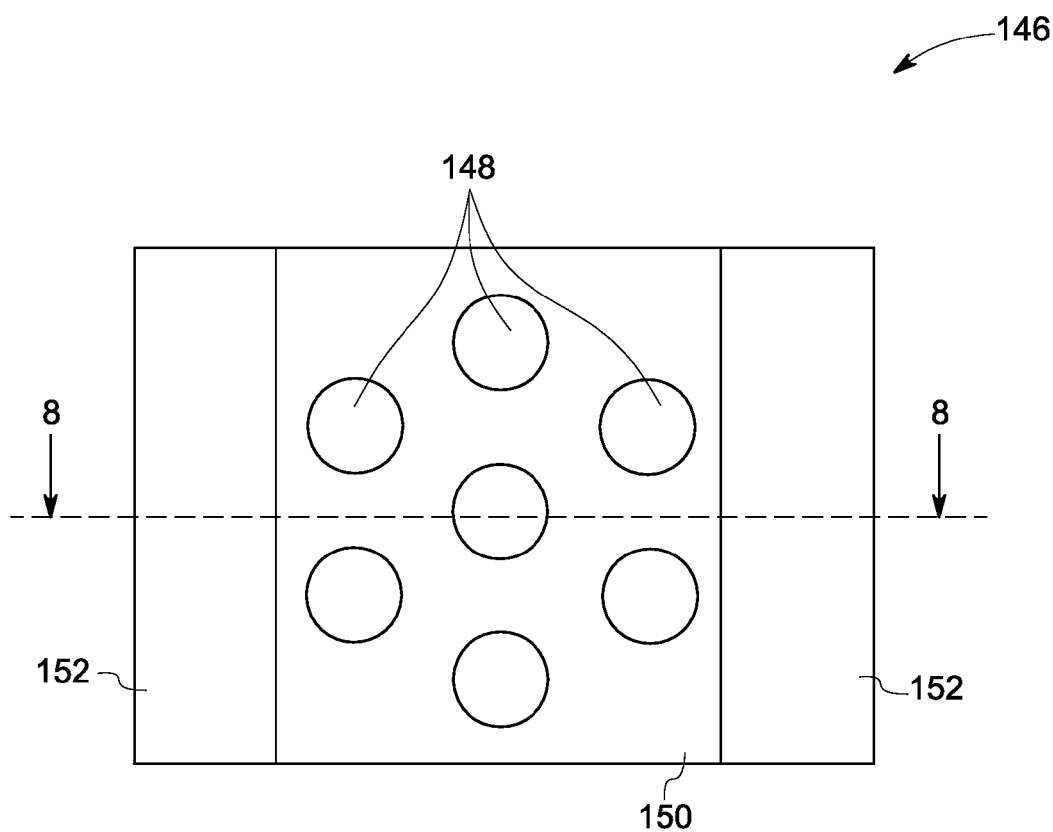
FIG. 7 is a top view of a sensing device having an electrode with plurality of holes.
Figure 8:
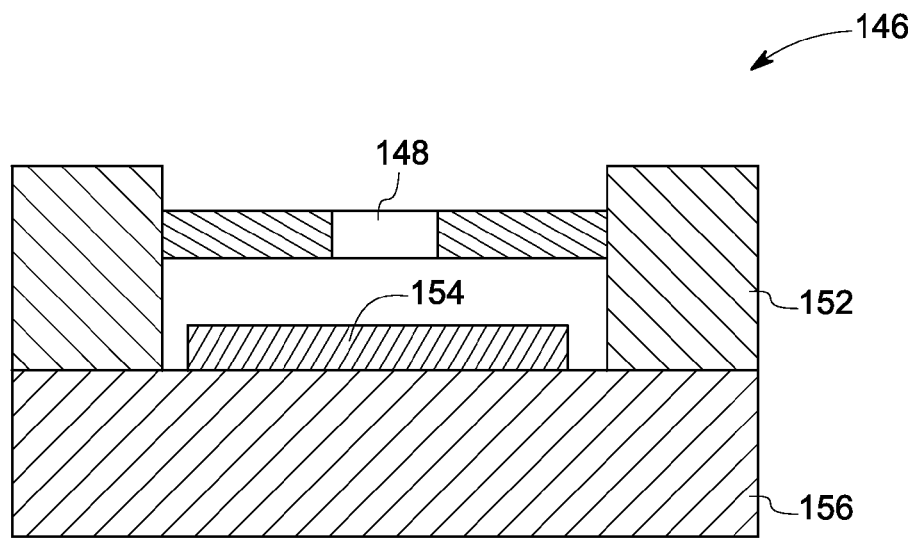
FIG. 8 is a side view of the sensing device of FIG. 7.

FIG. 7 illustrates a top view of an embodiment of a sensing device 146 that may be employed in the present technique. The sensing device 146 includes a plurality of holes 148 on a top electrode 150 supported between support structures 152. In one embodiment, the diameter of the holes may be in a range from about 5 nanometers to about 20000 nanometers. The top electrode 150 may have a geometric shape such as square, rectangular, circular, hexagonal, triangular, or any other polygon. FIG. 8 illustrates a cross-sectional side view of the sensing device 146. As illustrated the device also includes a bottom electrode 154. As with the top electrode 150, the bottom electrode may have different geometric shapes such as square, rectangular, circular, hexagonal, triangular, or any other polygon. Although not illustrated, the top and bottom electrodes 150 and 154 may or may not have planar surfaces. For example, there may be depression or protrusions on one or both the electrodes to tailor the gap of the sensing device. In one embodiment, the bottom electrode 154 may have a protrusion in a direction of the top electrode 150 such that the distance between the top electrode 150 and the bottom electrode 154 is smaller in the region having the protrusion.

Figure 9:
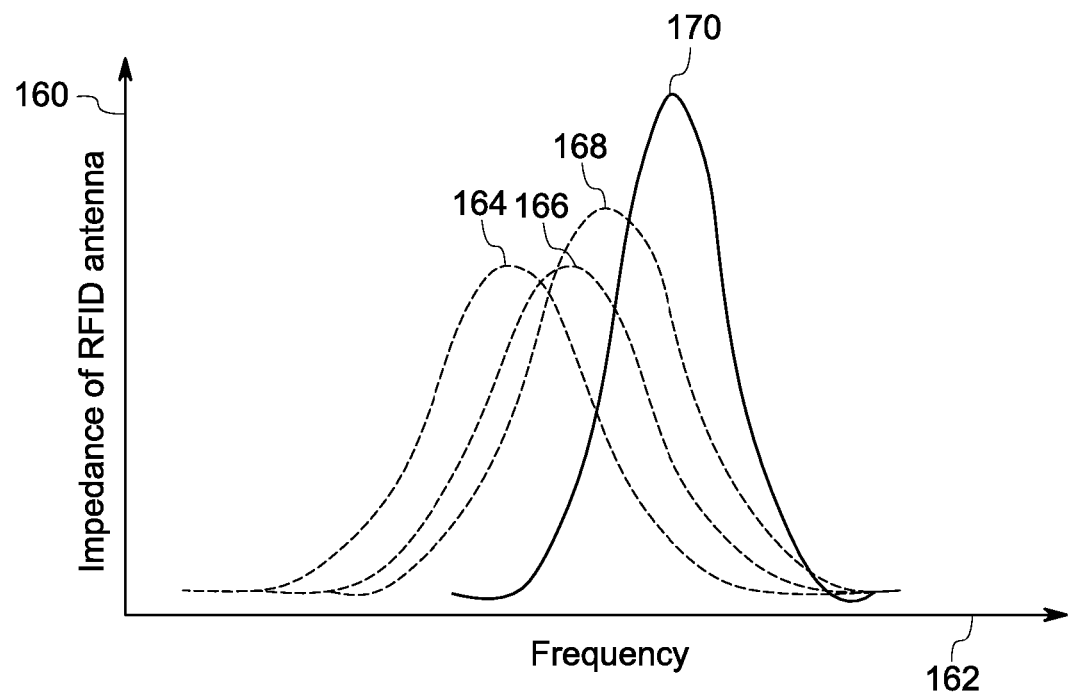
FIG. 9 is a graphical representation of a change in the signal of the sensing device upon detection of a physical, chemical, or biological parameter of interest.

FIG. 9 illustrates a change in the signal of the sensing device upon detection of a physical, chemical, or biological parameter of interest. In the presently contemplated embodiment, change in the resonance properties of the complex impedance of the antenna is measured. In the illustrated embodiment, the complex impedance response of the antenna is shown on ordinate 160, and the abscissa 162 represents the scanned frequency to measure the resonance of the RFID sensor. The graphs 164, 166, 168 and 170 represent the change in complex impedance of the sensor as a function of frequency when the sensor is exposed to different samples or a sample around the sensor changes its physical, chemical, or biological properties. As illustrated, the change in response of the sensor is reflected by the change in the width, shape, symmetry of shape, peak height, and peak position of complex impedance signal, that is the curves 164, 166, 168 and 170.

In certain embodiments, the circuit of the antenna is incomplete in the initial stage, when any species or parameter is not detected by the antenna up to a determined threshold. In these embodiments, the electrical circuitry of the antenna is physically incomplete due to the discontinuity created by the gap. In these embodiments, in the initial state, the resistance of the incomplete circuit of the antenna may be greater than or equal to about 1000 Ohms. The electrical circuitry of the antenna is completed when the species that is to be detected or a change in physical property of the sample affects the resistance and capacitance of the gap to bring the magnitude of the resonance above a determined threshold at the operating frequency range of the digital reader/writer. At this stage, the reader/writer is able to read or recognize the memory chip. The digital reader/writer writes a time sequence of data into memory chip. Non-limiting examples of physical properties that affect the response of the sensor are ionizing radiation (e.g. gamma radiation, beta radiation, X-rays) dose, liquid conductivity, temperature, pressure, acceleration, or combinations thereof.

In one embodiment, addition of a sensing device results in the creation of a resonance structure, and the sensing device affects the resonance of the structure as a function of the environmental change. If resonance is changed due to attached sensing device to the RFID, such that the resonance falls outside the frequency range of writing the digital data for the sensor, certain values of the sensor response are not written into the memory chip, thus permanently storing time sequence data.

FIGS. 10-12 illustrate the concept of appearance or disappearance of digital ID reading with a digital reader/writer. The center point represents the operating frequency range of a digital writer/reader. The operating frequency range of the digital writer/reader may be from about 120 KHz to about 5.8 GHz. In one example, the center point may be at about 13.56 MHz frequency. As illustrated in FIG. 10, the complex impedance response of the antenna at frequency F 176 drawn on ordinate 172, and the abscissa 174 is represented by the graph 178. In the illustrated embodiment of FIG. 10, the resonance magnitude of the antenna is too weak (graph 180) due to the sensing device response. In this case, the writer cannot detect the RFID sensor and hence, does not write portions of the time sequence into memory chip. As illustrated in FIG. 11, the impedance/resonance response (graph 182) of the sensor has been shifted due to the sensor response and is too far from the center point as indicated by the arrow 184 due to the response of the sensing device, the reader/writer cannot see the RFID sensor and does not write portions of the time sequence into memory chip. Referring now to FIG. 12, the resonance is far from the center point 176 as illustrated by the arrow 188 before sensor response and overlaps with the center point upon sensor response (186), the reader/writer sees the RFID sensor and writes portions of the time sequence into memory chip. Accordingly, the reader/writer is unable to detect the RFID sensor and therefore, does not write portions of the time sequence into memory chip.

Figure 13:
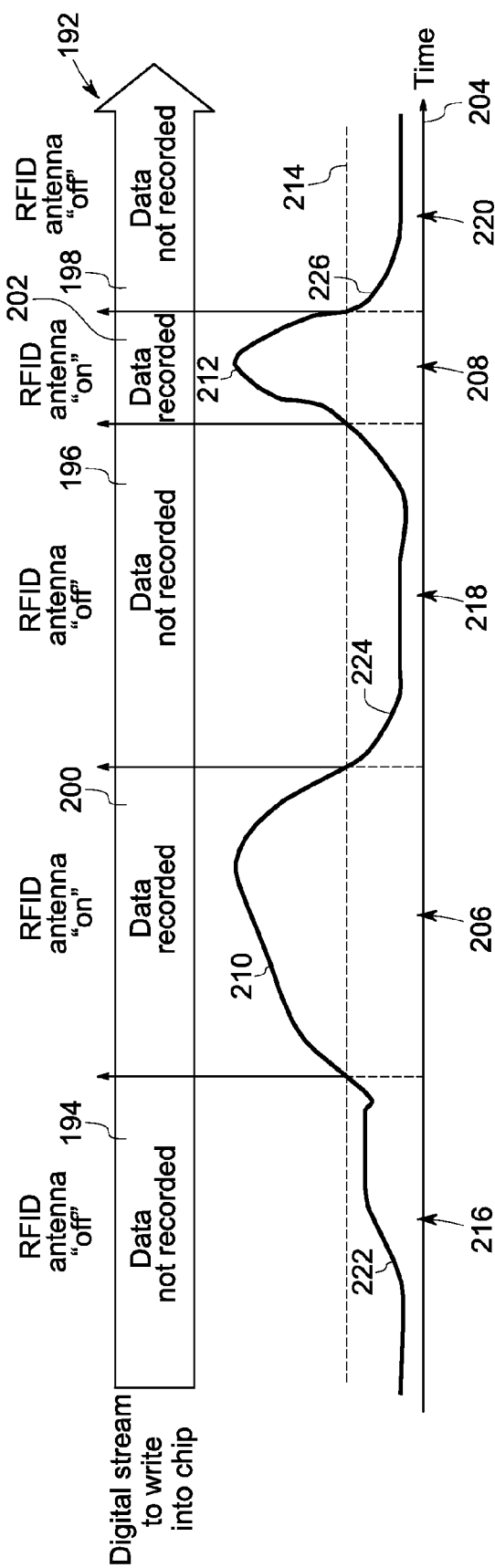
FIG. 13 is a graphical representation of detection and recording of sensing events by a sensor when the sensor is physically located in the measurement environment.

FIG. 13 illustrates digital data stream 192 having sequences 194, 196 and 198 that are not written by the writer onto the memory chip, whereas sequences 200 and 202 are written by the writer onto the memory chip. The digital data stream is generated by the reader/writer. The sensor is physically located in the measurement environment. For time-critical applications where there is a need to track the time of exposure that exceeds a predetermined limit, digital data is recorded onto the chip only when a parameter of interest exceeds the threshold. The abscissa 204 represents time. The data stream is recorded for time intervals 206 and 208 for which values 210 and 212, respectively, of the parameter of interest are above the threshold value 214. Whereas, the data stream is not recorded for time intervals 216, 218 and 220 for which the values 222, 224 and 226, respectively, of the parameter are below the threshold value 214.

The values recorded in the memory chip contain digital data stream related to the times of the recorded events and the sensing values of the response of the gap-based device. The sensing values of the response of the gap-based device are correlated to the concentrations or levels or magnitudes of physical, chemical, or biological parameter of interest in the measured sample around the sensor.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A sensor, comprising:
    at least one sensing device comprising a first electrode and a second electrode, and a gap defined as a distance between one or more facing inner surfaces of the first and second electrodes, wherein the gap distance at least in part determines a threshold of one or more sensed parameters; and
    an antenna in operative association with the sensing device, wherein the first electrode, the second electrode, or both, have one or more surfaces on which a dielectric material is provided that is adapted to prevent the electrode from shorting out when exposed to a conductive fluid.

2. A sensor, comprising:
at least one sensing device comprising a first electrode and a second electrode, and a gap defined as a distance between one or more facing inner surfaces of the first and second electrodes, wherein the gap distance at least in part determines a threshold of one or more sensed parameters; and
an antenna in operative association with the sensing device, wherein the sensor is disposed on a silica surface that is free of any surface modifications to enable nonspecific binding of molecules, molecular assemblages, or both.

3. A radio frequency based sensor, comprising:
a sensing gap defined by two or more electrodes; and
an antenna in operative association with the sensing gap and the electrodes, wherein a sensing signal is identified by appearance or disappearance of a digital identification through a digital reader/writer.

4. The sensor of claim 3, wherein the gap between the inner surfaces of the first and second electrodes is in a range of about 5 nm to about 10000 nm.

5. The sensor of claim 3, wherein a portion of the antenna is configured to function as the sensing device.

6. The sensor of claim 5, wherein the gap is defined by the distance between windings of the antenna.

7. The sensor of claim 3, wherein the sensor is configured for detection of chemical species, or biological species, or physical properties, or combinations thereof.

8. The sensor of claim 3, wherein the first and second electrodes comprise a channel, or an interdigital electrode structure, or a three dimensional electrode structure, or combinations thereof.

9. The sensor of claim 3, wherein the gap comprises a zero-dimensional gap structure, a one-dimensional gap structure, a two-dimensional gap structure, a three-dimensional gap structure.

10. The sensor of claim 3, wherein a shape of the gap comprises a slot, an array of slots, a morphology-induced shape, a serpentine shape, a coil, a fractal, or combinations thereof.

11. The sensor of claim 3, wherein the gap is substantially free of an electrode material, or a sensing material, or both.

12. The sensor of claim 3, wherein the gap comprises air, a dielectric material, a metal, a semiconductive material, an organic electronic material, a biological sensing material, an organic sensing material, or an inorganic sensing material.

13. The sensor of claim 12, wherein the sensing material comprises nanowires, nanofibers, nanoparticles, formulated materials with functional additives, doped conjugated polymers, inorganic materials, organic materials, polymeric materials, biological materials, living cells, biological molecule receptors, antibodies, aptamers, nucleic acids, biological molecules functionalized with metal particles, biological molecules functionalized with polymer particles, biological molecules functionalized with silica particles and any other known sensing materials and their combinations that produce detectable change in resistance and/or capacitance upon chemical, biological, and/or physical changes around the sensing device.

14. The sensor of claim 3, wherein an electrode material comprises metal, copper, aluminum, gold, silver, alloys of copper, alloys of aluminum, alloys of gold, conducting polymer, doped polyacetylene, doped polyaniline, doped polythiophene, carbon nanotubes, carbon fibers, carbon particles, carbon paste, conducting inks, or combinations thereof.

15. The sensor of claim 3, wherein an electrical resistance of the electrode material is less than about 100 ohms.

16. The sensor of claim 3, wherein the sensing device is physically disposed on the antenna.

17. The sensor of claim 3, wherein the sensor is a wireless sensor, a wired sensor, an electronic sensor, an sensor, a radio frequency based sensor, or combinations thereof.

18. The sensor of claim 17, wherein the radio frequency based sensor comprises a radio frequency identification (RFID) tag.

19. The sensor of claim 3, wherein the radio frequency based sensor is a radio frequency identification tag with an analog input into a memory chip.

20. The radio frequency based sensor of claim 3, wherein a complex impedance of the antenna changes as a function of frequency.

21. A radio frequency based sensor, comprising:
a sensing gap defined by two or more electrodes; and
an antenna in operative association with the sensing gap and the electrodes, wherein a sensing signal is identified by appearance or disappearance of a digital identification through a digital reader/writer and magnitude of the sensing signal is written onto the memory chip along with the time associated with this sensor magnitude.

22. A radio frequency based sensor, comprising:
a sensing gap defined by two or more electrodes; and
an antenna in operative association with the sensing gap and the electrodes, wherein a sensing signal from a sensor attached to the analog input of the memory chip is written onto the memory chip along with the time associated with this sensor signal.

23. A method of making a sensor, comprising:
providing an antenna having one or more turns;
forming a sensing gap comprising first and second electrodes and defined by a distance between one or more facing inner surfaces of the first and second electrodes, wherein the gap distance at least in part determines a threshold of one or more sensed parameters, and wherein the sensing gap is in operative association with the antenna, wherein forming the first electrode and the second electrode comprises self assembly, roll-to-roll process, lithography, liquid deposition, milling, or combinations thereof.

24. A sensor, comprising:
at least one sensing device comprising a first electrode and a second electrode, and a gap defined as a distance between one or more facing inner surfaces of the first and second electrodes, wherein the gap distance at least in part determines a threshold of one or more sensed parameters, wherein the first electrode, the second electrode, or both, have one or more surfaces on which a dielectric material is provided that is adapted to prevent the electrode from shorting out when exposed to a conductive fluid; and
an antenna in operative association with the sensing device.

25. A sensor, comprising:
at least one sensing device comprising a first electrode and a second electrode, and a gap defined as a distance between one or more facing inner surfaces of the first and second electrodes, wherein the gap distance at least in part determines a threshold of one or more sensed parameters; and
an antenna in operative association with the sensing device, wherein the sensor is disposed on a silica surface that is free of any surface modifications to enable nonspecific binding of molecules, molecular assemblages, or both.

26. A radio frequency based sensor, comprising:

a sensing gap defined by two or more electrodes; and an antenna in operative association with the sensing gap and the electrodes, wherein a sensing signal is identified by appearance or disappearance of a digital identification through a digital reader/writer.

* * * * *